United States Patent [19]

Avera, Jr.

[11] 4,243,884
[45] Jan. 6, 1981

[54] PROBE ASSEMBLY

[75] Inventor: C. Bert Avera, Jr., Cincinnati, Ohio

[73] Assignee: Actus, Inc., Florence, Ky.

[21] Appl. No.: 959,243

[22] Filed: Nov. 9, 1978

[51] Int. Cl.² ............................................. G01T 1/20
[52] U.S. Cl. ............................ 250/361 R; 128/654; 128/659; 250/363 S
[58] Field of Search ...................... 250/361 R, 363 S; 128/653, 654, 659, 691

[56] References Cited

U.S. PATENT DOCUMENTS 4,092,980  6/1978  Frank et al. ................... 250/363 S Primary Examiner—Davis L. Willis
Attorney, Agent, or Firm—Fleit & Jacobson

[57] ABSTRACT

A hand-held probe assembly, suitable for monitoring a radioactive fibrinogen tracer, is disclosed comprising a substantially cylindrically shaped probe handle having an open end. The probe handle is adapted to be interconnected with electrical circuitry for monitoring radioactivity that is sensed or detected by the probe assembly. Mounted within the probe handle is a probe body assembly that includes a cylindrically shaped probe body inserted through the open end of the probe handle. The probe body includes a photomultiplier tube that is electrically connected with a male connector positioned at the rearward end of the probe body. Mounted at the opposite end of the probe body is a probe head which supports an optical coupler therewithin. The probe head is interconnected with a probe cap which supports a detecting crystal. The probe body assembly, which consists of the probe body, the probe head, and the probe cap is supported within the probe handle by means of a pair of compressible O-rings which permit the probe assembly to be freely rotatable, preferably through 360°, within the probe handle and removable therefrom without requiring any disassembly.

32 Claims, 6 Drawing Figures

U.S. Patent  Jan. 6, 1981  Sheet 1 of 2  4,243,884
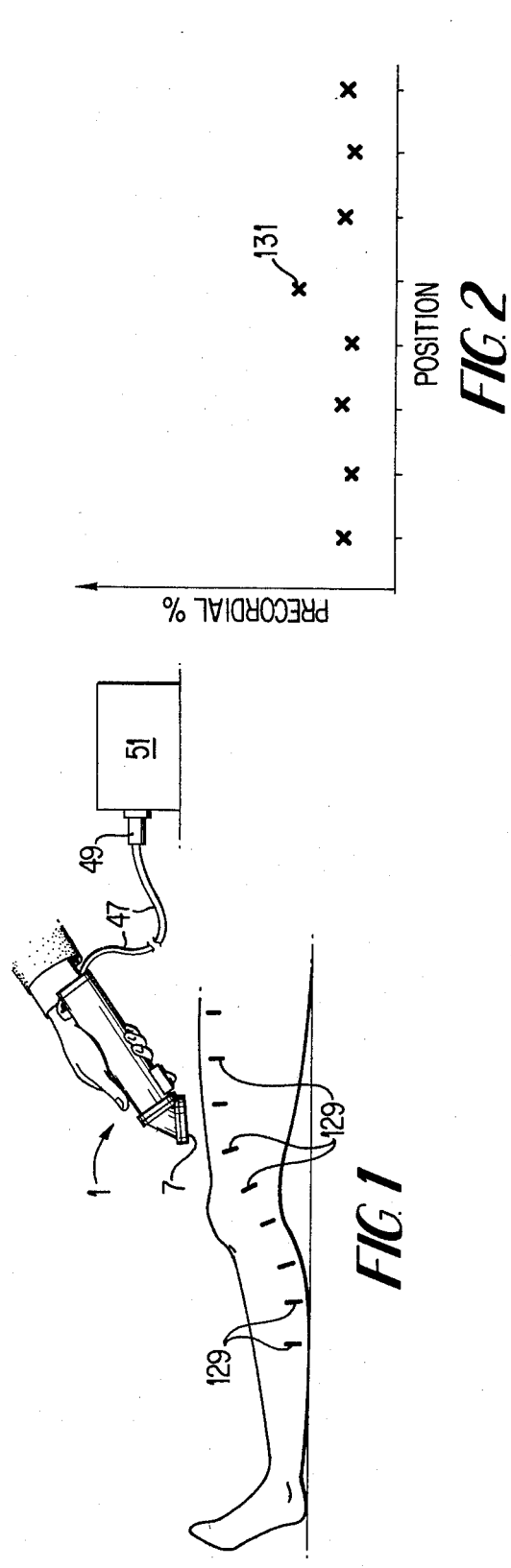
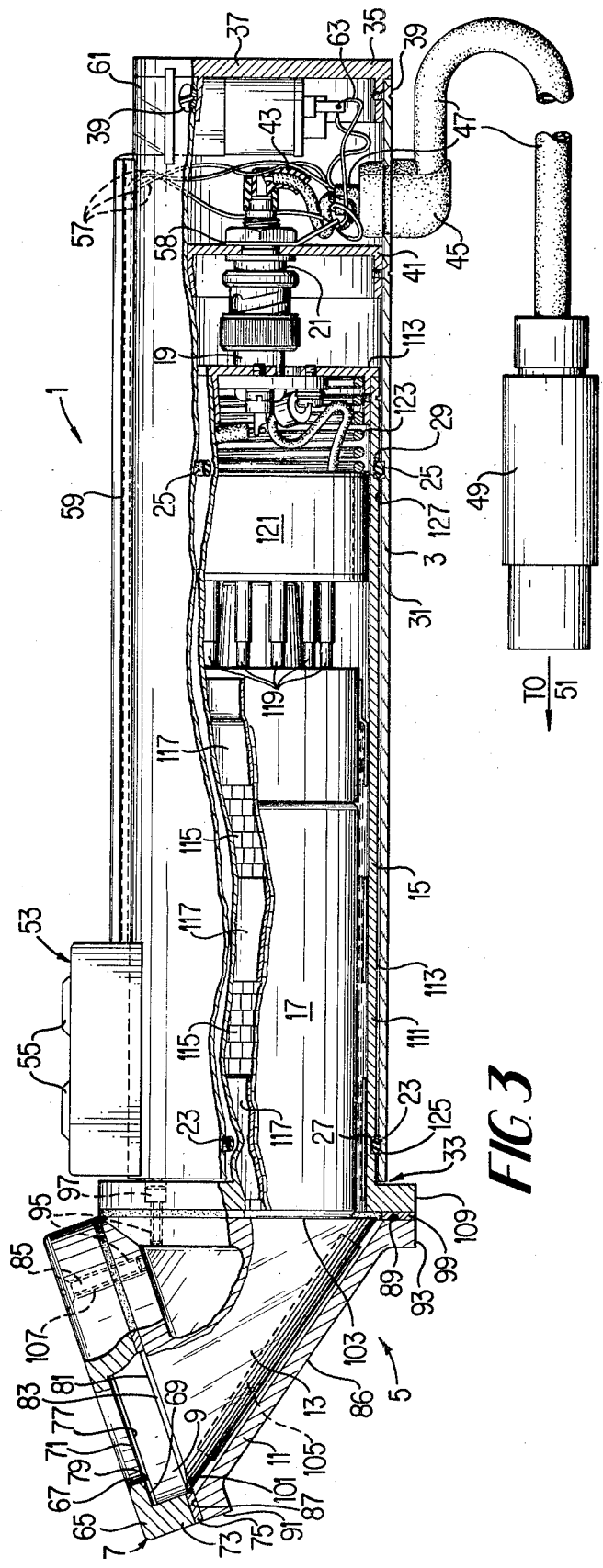

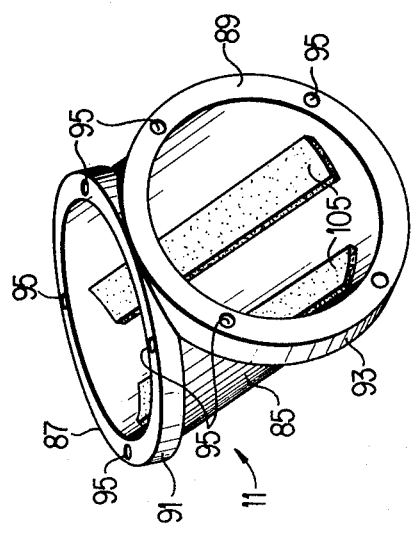
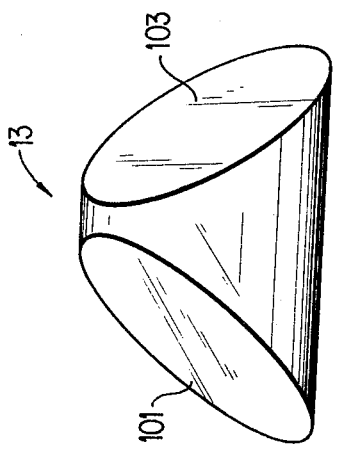
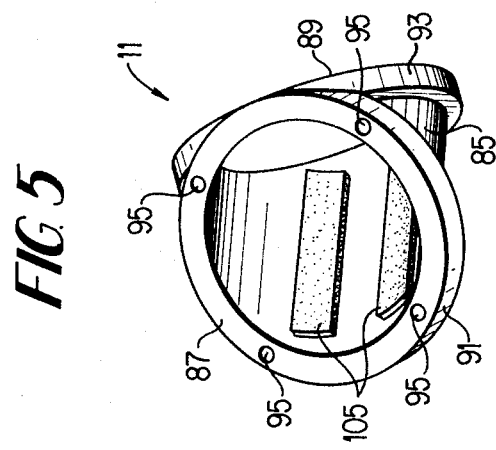

PROBE ASSEMBLY

BACKGROUND OF THE INVENTION

The present invention relates to a probe assembly for detecting radiation, such as nuclear and X-ray radiation. In particular, the probe assembly has particular utility as a fibrinogen monitor probe assembly, although broader uses, such as a detector for thyroid uptake, should be readily apparent.

Several devices are known which are designed for the early detection of deep vein thrombosis. The devices include hand-held detector probes sensitive to radiation, and electronics to convert the detected radiation to meaningful data. Typically, such devices are operated in the leg region.

In this procedure, an I-125 labeled fibrinogen is intravenously injected into the patient. Then, the leg is marked with a map to guide the operator in sequentially positioning the detector probe. Once the injected fibrinogen tracer has dispersed throughout the body (in the neighborhood of three hours), radiation readings are taken with the deep vein thrombosis detection apparatus. First, a precordial count is made, and then, with the markings previously positioned on the leg, radiation counts are made along the leg, generally as a percent of the precordial count, and the readings are plotted. Localized excesses of the radioactive fibrinogen tracer are indicative of clot formations.

Hand-held detector probes are known in the art. Such probes are generally cylindrically shaped, not unlike ordinary cylindrically shaped flashlights, and include a detecting head at one end, inclined to the major axis of the cylinder, and interconnected with electrical circuitry for monitoring the radioactive fibrinogen tracer. Such prior art hand-held probes have a number of disadvantages. For example, the probe head is generally fixed in position with respect to the probe handle and the head is not rotatable with respect to the handle. This makes the correct positioning of the probe head adjacent to various areas of the body sometimes difficult.

The probe heads of the prior art, such as those described above, are oftentimes difficult to service in that the head is a unitary one-piece assembly that requires mechanical disassembly in order to work on the internal mechanical or electrical apparatus.

Further, prior art probe heads have no indicator or meter that is mounted directly on the probe handle. Thus, the operator cannot visually determine the maximum precordial count, nor the position where the clot formations occur in the body, without also viewing a remote electronic monitor assembly that is electrically connected with the probe handle.

SUMMARY OF THE INVENTION

It is an object of the present invention to provide a convenient, simple, and accurate radiation monitor probe assembly, particularly a hand-held fibrinogen monitor probe assembly, capable of easy repair and great maneuverability.

In particular, it is an object of the present invention to provide a probe assembly having a probe head interconnected with a probe handle, such that the probe head is freely rotatable with respect to the handle.

It is further an object of the present invention to provide a hand-held fibrinogen monitor probe assembly comprising a two-piece, pull-apart assembly that is easily assembled and disassembled. One piece of the two-piece assembly comprises a cylindrically shaped probe handle that is interconnected electrically with a remote electronic monitoring apparatus, the latter being conventionally known in the art. The other piece of the probe assembly comprises a probe body assembly. The probe body assembly comprises a cylindrically shaped probe body that is supported within the probe handle. Connected with the probe body is a probe head and a probe cap, all of which are fixedly connected together and which can be easily inserted in, and removed from, the probe handle.

It is a further object of the present invention to support the probe body assembly within the handle by supporting means that maintains the probe body assembly secure within the handle, yet can be easily removed manually without time-consuming disassembly.

Still further, it is an object of the present invention to provide supporting means for supporting the probe body assembly within the probe handle, comprising compressible O-rings that engage the inside of the probe handle to maintain the probe body assembly securely, yet freely and continuously rotatable, preferably throughout a full 360° movement within the probe handle. This enables the operator to use the probe in a variety of different and difficult-to-reach positions. It is also an object of the present invention to include, as part of the probe body assembly, a probe cap, supporting a crystal detector, wherein the probe cap face is inclined to the major axis of the probe handle, preferably between 15° and 30°, and is freely rotatable so that the operator can insure good contact between the probe cap face and the human body.

Still further, it is an object of the present invention to provide the probe handle with an indicator or scanning meter that provides instantaneous visual read-out to the operator, so that the operator can determine the optimum precordial count and where a blood clot occurs. This enables the operator to ensure that accurate readings are obtained.

These and other objects of the invention will be readily apparent when reference is made to the detailed description taken in conjunction with accompanying drawings.

BRIEF DESCRIPTION OF THE DRAWINGS

FIG. 1 schematically depicts the operation of a hand-held fibrinogen monitor probe assembly;

FIG. 2 depicts a graph to determine the clot points of a patient;

FIG. 3 is a cross-sectional view of the fibrinogen monitor probe assembly of the present invention;

FIG. 4 is a perspective view of the optical coupler of the present invention;

FIGS. 5 and 6 are perspective views of the probe head of the present invention.

DETAILED DESCRIPTION OF THE DRAWINGS

The invention relates to a fibrinogen monitor, or other radiation monitor, probe assembly 1 comprising a two-piece assembly that is particularly suitable as a hand-held assembly. One piece comprises the probe handle 3 and the second piece comprises the probe body assembly 5. The probe body assembly 5 comprises a probe cap 7 which supports a detecting crystal 9. The probe cap 7 is mounted fixedly onto a probe head 11. The probe head 11 supports an optical coupler 13. The probe head 11 is fixedly connected to a probe body 15. The probe body 15 supports a photomultiplier tube 17 which is electrically interconnected with a male electrical connector 19. The male connector 19 mates with a female connector 21 which is part of the probe handle 3. The probe cap 7, probe head 11, and probe body 15 are fixedly interconnected and are supported within the probe handle 3 by means of a pair of elastic, compressible O-rings 23,25, which are mounted in peripheral slots 27,29 in the probe body 15. The probe body 15 is totally supported within the probe handle 3 by means of the O-rings 23,25 and is freely and continuously rotatable throughout 360° within the probe handle 3. No other inter-connection between the probe body 15 and probe handle 3 is provided, except for the connection between the male 19 and female 21 connectors. The probe body assembly 5 can easily be removed from the probe handle 3 by simply pulling the probe handle 3 and probe body assembly 5 apart manually, thus enabling any defective parts to be easily repaired or replaced.

The probe handle 3 is adapted to easily be held by the technician, as shown in FIG. 1, and comprises a cylindrical tube 31 having an open end 33 and a closed end 35. As shown in FIG. 3, the closed end 35 is a separate cap 37 secured to the probe handle 3 by screws 39. Mounted within the probe handle 3, near the closed end 35, is a plate 41 that includes a female connector 21, similar to a signal jack. The female connector 21 is adapted to receive a male connector 19 associated with the probe body 15, to be described further below; the female connector 21 extends through the plate 41, is connected thereto, and is electrically connected with a coaxial conductor 43 which is within cable 47. Cable 47 extends through the strain relief bushing 45, and is connected to cable connector 49 for connection to conventional electronic monitoring circuitry 51 that monitors the output. The electronic monitoring circuitry forms no part of the present invention. It should be recognized that the female connector 21 and the male connector 19 can be interchanged such that the female connector 21 is associated with the probe body 15, and the male connector 19 associated with the plate 41.

Mounted on the probe handle 3 is a switch assembly 53 which is positioned near the forward end of the probe handle 3 and provided with finger controlled buttons, or switches 55 which can easily be operated by the technician to control various functions of the electronic monitoring circuitry, such as the count and print functions. The switch assembly 53 is connected by wires 57 which are connected with a ground plate 58 and through the cable 47. The wires 57 are guided in a wire enclosing tunnel 59 at the top part of the handle 3.

Mounted at the rear of the probe handle 3 is an indicator meter 61 which provides an indication of the electrical output from the probe body assembly 5, to be described further below. The indicator meter 61 is conventionally interconnected by wires 63 to the ground plate 58 and through the cable 47 to receive an electrical output from the electronic monitoring circuitry 51. Any conventional visual read-out, such as a movable dial, can be employed as the meter 61.

Turning to the probe body assembly 5, there is provided a probe cap 7 that is short-right cylindrically shaped with an annular cross-section. The annular rim 65 is substantially L-shaped with one leg of the "L" 67 extending inwardly. Mounted at the inside 69 of the L-shaped lip 65 is a probe window 71. The other leg 73 of the L-shaped annular cylinder is adapted to be matingly engaged, through a gasket 75, to the probe head 11, described further below.

Mounted within the probe cap 7 is a crystal detector 9, such as a Harshaw 6HA2M. The detector 9 is a photoluminescent detector crystal that converts radioactivity to light. The crystal 9 is cylindrical in shape and has one face 77 positioned, by means of a gasket 79, adjacent the probe window 71. The other face 81 of the crystal 9 is positioned adjacent the optical coupler 13, to be described further below, and mates with the optical coupler 13 through a conventional optical coupling compound 83. The probe cap 7 is fixedly secured to the probe head 11 by means of screws 85 that are mounted in the annular peripheral cap portion 65 through holes 107.

Note that the probe cap 7 could be interchanged with a deeper cap to hold a thicker crystal having the same diameter. This could become necessary when using a higher energy gamma ray source that is injected into the patient. It is known that the greater the energy level to be detected, the thicker the crystal must be in order to trap the gamma rays inside the crystal. Typically, the radiation level is 30 kev. However, in detecting cobalt or iron, the radioactive output is closer to 600 to 1,000 kev, thus requiring thicker crystal detectors.

Connected to the probe cap 7 is a probe head 11. The probe head 11, as shown in FIGS. 3, 5, and 6, is essentially a cylindrical tube 85 having inclined end faces 87, 89. The angle of inclination of the end faces 87, 89 is preferably 70° with respect to each other. Each end face 87, 89 of the probe head 11 comprises an annular flange 91, 93 with openings 95 therethrough for receiving a screw 85, 97. The end face flange element 91 adjacent the probe cap 7 mates with the probe cap 7 through a gasket 75. The probe head flange 93 adjacent the opposite end of the probe head 11 mates with the probe body 15, to be described further below, likewise through a gasket 99 and also includes openings 95 for a screw connection 97 therebetween. Thus, it can be seen that the probe cap 7, probe head 11 and probe body 15 are fixedly secured together to form a unitary probe body assembly 5. Note that the probe head 11 is symmetrical, and either flange 91, 93 can be connected adjacent the probe cap 7 and probe body 15.

Positioned within the probe head 11 is an optical coupler 13. The optical coupler is a cylindrical, transparent rod, preferably a clear acrylic rod having end faces 101, 103 angled at 70° with respect to each other. It is preferable that the end faces 101, 103 of the optical coupler 13 are at the same angle as the end faces 87, 89 of the probe head 11. The end face angles of the optical coupler 13 and probe head 11 can range from 0° to 90°, with a 60° to 75° angle as desirable, and a 70° angle as the optimum. Likewise the face 77 of the crystal 9, when the probe cap 7 is connected to the probe head 11, will be disposed at the same angle, but with respect to a plane perpendicular to the major axis of the probe handle 3. That is, the face 77 of the crystal 9 can be disposed between 0° and 90°, but preferably between 15° and 30° with respect to the major axis of the probe handle 3, with 20° being the optimum. The optical coupler 13 preferably has no reflecting coating and uses total internal reflection, i.e., reflection without any loss. The optical coupler 13 is supported within the probe head 11 by a pair of pads 105 that are glued, or otherwise secured, to the probe head 11.

It is thus seen that when the probe cap 7 is positioned adjacent a radioactive source, such as an intravenously injected I-125 source, the radioactivity is converted by the crystal detector 9 into light which is coupled by internal reflection from the optical coupler 13 to the photomultiplier tube 17 mounted in the probe body 15, as described further below. It should also be noted that under certain operating conditions the probe cap 7 can be mounted directly to the probe body 15, thus omitting the optical coupler 13 and probe head 11. The openings 107 on the probe cap periphery are designed to mate with openings mounted in the probe body flange 109.

The probe body 15 is inserted through the probe handle opening 33, as depicted in FIG. 3, and comprises a cylindrical tube 111 having an outer diameter slightly less than the inner diameter of the probe handle 3 so as to define an annular space 113 therebetween. One end of the probe body 15 has an annular flange element 109 that mates, through a gasket 99, with the flange 93 of the probe head 11. Screw connections 97 are provided for physically connecting the probe head flange 93 and probe body flange 109.

The opposite end 113 of the probe body 15, i.e., the closed end, has attached thereto a male electrical connector 19. When the probe body 15 is inserted in the probe handle 3, the male connector 19 mates with the female connector 21 to provide an electrical connection. The male connector 19 is free to rotate within the female connector 21 when the probe body 15 is rotated within the probe handle 3. As discussed above, the female connector 21 and male connector 19 can be reversed.

Mounted within the probe body is a photomultiplier tube 17 that converts the light coupled by the optical coupler 13 into an electrical output. A typical photomultiplier tube 17 that can be used in the present invention is the RCA 6199. Surrounding the photomultiplier tube 17 is a basket-woven magnetic shield 115 that is held on with plastic electrical tape 117. The magnetic shield 115 is of the Metshield fabric manufactured by Allied Chemical Corporation. It should be noted that the electrical tape 117 may be omitted if insufficient space between the probe body 15 and the magnetic shield 115 exists.

Outlet leads 119 from the photomultiplier tube 17 are provided and are electrically connected, through a divider board assembly 121, with the male connector 19. Electrical components, such as resistor, capacitors, etc., can be provided in the divider board 121 to electrically operate on the output of the photomultiplier tube 17, depending on the particular electrical measurement desired, as is conventionally known. A coil spring 123 is provided so that when the device is completely assembled, good optical contact between the photomultiplier tube 17 and the optical coupler is assured.

The probe body 15 is supported within the probe handle 3 by means of a pair of elastic and compressible O-rings 23, 25. The O-rings 23, 25 are supported within circumferential grooves 27, 29 on the probe body 15 adjacent each end of the probe body 15, and are associated with and are part of the probe body assembly 5.

The first O-ring 23, when inserted into the probe handle 3, associates with a groove 125 in the inner periphery, or wall 127, of the probe handle 3. The second O-ring 25 abuts against the inner periphery of the probe handle 3 without accommodation into any groove of the probe handle 3. Thus, the O-ring 25 is compressed between its circumferential groove 29 in the probe body 15, and the inner wall 127 of the probe handle 3. The O-rings 23, 25 enable the entire probe body assembly 5 to be securely positioned within the probe handle 3, and yet easily be removed manually by the technician in order to repair the assembly. Further, the O-rings 23, 25 are designed to enable the probe body assembly 5 to freely and continuously be rotatable throughout 360° within the probe handle 3. This permits the technician to selectively position the probe cap 7 at various positions on the body, as shown in FIG. 1, without twisting the probe handle 3. That is, the probe handle 3 always remains in its optimum position, so that the indicator 61 can be easily read when measurements are being taken, and the switches 55 remain in an easily accessible position for the operator to manipulate.

It should be noted that the O-ring 25 may be eliminated. In such case, the engagement between the male connector 19 and the female connector 21 can provide a support, or bearing, for the rear portion of the probe body 15 within the probe handle 3. On the other hand, additional O-rings may be employed to support the probe body 15 within the probe handle 3.

It is not essential that the probe body assembly 5 be rotatable throughout a full 360°. Stop means may be provided to limit the rotatability to somewhat less than 360°. It is, however, essential that the probe body assembly 5 be freely rotatable within the range of rotation that is provided.

In operation, various markings 129 are made on the patient's body, such as the leg region. Reference should be made to copending U.S. Pat. Application Ser. No. 919,218, filed on June 26, 1978, and assigned to the same assignee as the present invention, which describes the methods of marking the patient's body for placement of the probe assembly 1 thereon. This copending application is incorporated herein by reference.

The probe assembly 1 is positioned by the technician at a number of points 129 along the patient's body, and readings are taken and graphed at these various points, as shown in FIG. 2. When the probe assembly 1 is positioned at a particular point that has a blood clot, the radioactivity will build up at that point and the output signal is increased. This is shown at plotting point 131 in FIG. 2.

Above, a specific embodiment of the present invention has been described. It should be appreciated, however, that this embodiment was described for purposes of illustration only, and is in no way intended to limit the scope of the present invention. Rather, it is the intention that the present invention be limited only as defined in the appended claims.

I claim

1. A hand-held radiation monitor probe assembly comprising a substantially cylindrically shaped probe handle having an open end, a substantially cylindrically shaped probe body positioned within said probe handle through the open end of the probe handle, supporting means for supporting said probe body within said probe handle, wherein said probe body is freely rotatable within said probe handle, and removable therefrom, a probe head fixedly connected to said probe body, an optical coupler supported within said probe head, a detecting crystal for detecting radiation and for converting the radiation to light, and means for supporting said detecting crystal adjacent said optical coupler, wherein a face of said detecting crystal is at an angle with respect to the major axis of the cylindrically shaped probe body.

2. The probe assembly of claim 1, wherein said supporting means for supporting said probe body within said probe handle comprises a first elastic compressible O-ring surrounding said probe body and mounted in a first circumferential groove in the probe body, said first O-ring engageable with a circumferential groove in an inner wall of the probe handle for retaining said probe body within said probe handle and for enabling rotational movement of said probe body within said probe handle.

3. The probe assembly of claim 2, wherein said supporting means for supporting said probe body within said probe handle further comprises a second elastic compressible O-ring surrounding said probe body, spaced apart from said first O-ring, and mounted in a second circumferential groove in the probe body, said second O-ring engageable with the inner wall of the probe handle.

4. The probe assembly of claim 3, wherein said first and second O-rings are spaced apart from each other adjacent opposite ends of the probe body.

5. The probe assembly of claim 3, wherein the overall diameter of the probe body and O-ring is greater than the inner diameter of the probe handle.

6. The probe assembly of claim 3, wherein said probe body includes a photomultiplier tube mounted therein, a first electrical connector mounted at an end of the probe body remote from the probe head, and means for electrically interconnecting said photomultiplier tube with said first electrical connector.

7. The probe assembly of claim 6, wherein said probe handle comprises a second electrical connector mounted adjacent an end of said probe handle, wherein said first electrical connector mates with said second electrical connector in electrical contact when said probe body is positioned within said probe handle.

8. The probe assembly of claim 7 wherein said first electrical connector is a male connector and said second electrical connector is a female connector.

9. The probe assembly of claim 3, wherein said first and second O-rings each provide a light-tight seal.

10. The probe assembly of claim 9, wherein said first and second O-rings each provide an air-tight seal.

11. The probe assembly of claim 1, wherein said probe handle includes a meter for visual readout of the radioactivity level detected.

12. The probe assembly of claim 1, wherein said optical coupler comprises a transparent member for transmitting light without substantial loss.

13. The probe assembly of claim 12, wherein said transparent member is acrylic.

14. The probe assembly of claim 12, wherein said transparent member is free of reflecting coatings.

15. The probe assembly of claim 12, wherein said optical coupler comprises a cylindrical rod having inclined end faces.

16. The probe assembly of claim 15, wherein said end faces are inclined at substantially 70° with respect to each other.

17. The probe assembly of claim 1, wherein said probe head comprises a cylindrical tube having inclined end faces.

18. The probe assembly of claim 17, wherein said optical coupler comprises a transparent cylindrical rod having inclined end faces, and wherein the angles of inclination of the optical coupler end faces are substantially equal to the angles of inclination of the probe head end faces.

19. The probe assembly of claim 17, wherein said end faces are inclined at substantially 70° with respect to each other.

20. The probe assembly of claim 17, wherein said probe head comprises pad means in said tube for supporting said optical coupler.

21. The probe assembly of claim 1, wherein said means for supporting said detecting crystal adjacent said optical coupler comprises a substantially cylindrical probe cap having an annular base secured to said probe head, and a probe cap window, and wherein said detecting crystal is substantially cylindrically shaped and positioned within said probe cap.

22. The probe assembly of claim 1, wherein said probe handle includes cable means for electrically connecting said probe assembly with an electrical circuit for monitoring the radiation detected.

23. The probe assembly of claim 1, wherein said probe body is freely rotatable 360° within said probe handle.

24. A two-piece pull-apart fibrinogen monitor probe assembly comprising a substantially cylindrical probe handle, a substantially cylindrical probe body, detecting means for detecting radioactivity and for converting the radioactivity to light, means for fixedly connecting said detecting means to said probe body, supporting means for supporting said probe body within said probe handle for enabling said probe body to be freely rotatable within said probe handle, said probe body further comprising means for converting light to an electrical output, means for electrically connecting said probe body to said probe handle, and means for electrically connecting said probe handle to an electrical monitoring circuit.

25. The probe assembly of claim 24, wherein said supporting means for supporting said probe body within said probe handle comprises a first elastic compressible O-ring surrounding said probe body and mounted in a first circumferential groove in the probe body, said first O-ring engageable with a circumferential groove in an inner wall of the probe handle for retaining said probe body within said probe handle and for enabling rotational movement of said probe body within said probe handle.

26. The probe assembly of claim 25, wherein said supporting means for supporting said probe body within said probe handle further comprises a second elastic compressible O-ring surrounding said probe body, spaced apart from said first O-ring, and mounted in a second circumferential groove in the probe body, said second O-ring engageable with the inner wall of the probe handle.

27. The probe assembly of claim 24 wherein said probe handle includes an indicator means for visual readout of the radioactivity level to be detected.

28. A radiation monitor probe assembly comprising a substantially cylindrical shaped probe handle, detecting means for detecting radiation and for converting the radiation to light, and means for interconnecting said detecting means with said probe handle for enabling said detecting means to be freely rotatable with respect to the probe handle along the major axis of the probe handle.

29. The probe assembly of claim 28, wherein said detecting means comprises a detecting crystal having a substantially planar face disposed at an angle between 15° and 30° with respect to the major axis of said probe handle.

30. The probe assembly of claim 29 wherein said planar face is disposed at an angle of 20° with respect to the major axis of said probe handle.

31. The probe assembly of claim 28 wherein said probe handle includes an indicator means for visual readout of the radioactivity level to be detected.

32. The probe assembly of claim 28 wherein said detecting means is freely rotatable with respect to the probe handle throughout 360°.

* * * * *